(12) United States Patent
Sherrod et al.

(10) Patent No.: US 6,911,407 B2
(45) Date of Patent: Jun. 28, 2005

(54) NON-SLIP ABSORBENT ARTICLE (75) Inventors: Earle H. Sherrod, Appleton, WI (US); Daniel L. Ellingson, Appleton, WI (US); Stephen M. Campbell, Winneconne, WI (US); Thomas H. Roessler, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 107 days.

(21) Appl. No.: 10/034,816

(22) Filed: Dec. 27, 2001

(65) Prior Publication Data

US 2003/0124928 A1 Jul. 3, 2003

(51) Int. Cl.$^7$ ................................................. B32B 5/18
(52) U.S. Cl. ........................... 442/76; 442/79; 442/85; 442/86; 442/101; 442/422
(58) Field of Search ............................ 442/76, 79, 85, 442/86, 101, 289, 397, 422

(56) References Cited

U.S. PATENT DOCUMENTS

| | | |
|---|---|---|
| 349,784 A | 9/1886 | Cox |
| 1,633,951 A | 6/1927 | O'Toole |
| 1,641,029 A | 8/1927 | Gaudet |
| 2,187,676 A | 1/1940 | Biewen |
| 2,414,927 A | 1/1947 | Chapman |
| 2,771,613 A | 11/1956 | Markiewicz |
| 3,298,648 A | 1/1967 | Sepanski |
| 3,653,382 A | 4/1972 | Easley et al. |
| 3,657,745 A | 4/1972 | Hickman |
| 3,731,688 A | 5/1973 | Litt et al. |
| 3,738,359 A | 6/1973 | Lindquist et al. |
| 3,868,287 A | 2/1975 | Lewyckyj |
| 3,902,484 A | 9/1975 | Winters |
| 3,968,798 A | 7/1976 | Hokanson |
| 4,041,950 A | 8/1977 | Jones |
| 4,097,943 A | 7/1978 | O'Connell |
| 4,125,656 A | 11/1978 | Creamer |
| D253,985 S | 1/1980 | Bond |
| D255,197 S | 6/1980 | Brown |
| 4,285,075 A | 8/1981 | Nelson |
| 4,328,275 A | 5/1982 | Vargo |
| 4,379,192 A | 4/1983 | Wahlquist et al. |
| 4,439,474 A | 3/1984 | Sagel |
| 4,535,481 A | 8/1985 | Ruth-Larson et al. |
| 4,536,433 A | 8/1985 | Sagi et al. |

(Continued)

FOREIGN PATENT DOCUMENTS

| | | |
|---|---|---|
| CA | 2208905 A1 | 1/1998 |
| CA | 2208985 A1 | 1/1998 |

(Continued)

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

(Continued)

*Primary Examiner*—Arti R. Singh
(74) *Attorney, Agent, or Firm*—Scott A. Baum; John L. Brodersen; Sebastian C. Pugliese, III (57) ABSTRACT

Disclosed is an absorbent article useful for the following purposes without limitation: as a bed pad, a baby changing pad, a bib, a table cloth, or a painter's drop cloth. The absorbent article includes a vapor-permeable liquid-impermeable bottomsheet having an interior surface and an exterior surface, an absorbent structure positioned adjacent the interior surface, and a non-adhesive skid-resistant coating applied to the exterior surface such that the bottomsheet remains vapor-permeable after application of the coating. The non-adhesive skid resistant coating improves the ability of the absorbent article to remain in position without leaving residue on surfaces while leaving the absorbent article breathable.

10 Claims, 3 Drawing Sheets

U.S. PATENT DOCUMENTS

| | | | |
|---|---|---|---|
| 4,664,959 A | 5/1987 | Dagenais et al. | |
| 4,675,015 A | 6/1987 | Brown | |
| 4,712,258 A | 12/1987 | Eves | |
| D294,909 S | 3/1988 | Donnor | |
| 4,731,071 A | 3/1988 | Pigneul | |
| 4,772,281 A | 9/1988 | Armstead | |
| 4,792,024 A | 12/1988 | Morton | |
| 4,813,944 A | 3/1989 | Haney et al. | |
| 4,822,669 A | 4/1989 | Roga | |
| 4,834,739 A * | 5/1989 | Linker et al. | 604/385.04 |
| 4,850,991 A | 7/1989 | Nakanishi et al. | |
| 4,886,697 A | 12/1989 | Perdelwitz | |
| 4,900,377 A | 2/1990 | Redford | |
| 4,939,017 A | 7/1990 | Foxman | |
| 4,961,982 A | 10/1990 | Taylor | |
| 4,964,859 A | 10/1990 | Feldman | |
| 4,999,863 A | 3/1991 | Kane | |
| 5,011,480 A | 4/1991 | Gossens et al. | |
| D318,575 S | 7/1991 | Applebaum | |
| D322,003 S | 12/1991 | Hytry | |
| 5,114,774 A | 5/1992 | Maxim, Jr. | |
| 5,123,130 A | 6/1992 | Sanders | |
| 5,125,121 A | 6/1992 | Wroble | |
| 5,249,320 A | 10/1993 | Moretz et al. | |
| 5,252,374 A | 10/1993 | Larsonneur | |
| 5,282,283 A | 2/1994 | Atkin | |
| 5,294,258 A | 3/1994 | Jarrell | |
| 5,304,158 A | 4/1994 | Webb | |
| 5,318,107 A | 6/1994 | Bell | |
| 5,318,553 A | 6/1994 | Weeks et al. | |
| 5,375,271 A | 12/1994 | Frankel | |
| 5,379,558 A | 1/1995 | Mason, III | |
| 5,382,400 A | 1/1995 | Pike | |
| D358,734 S | 5/1995 | Paskwietz et al. | |
| 5,540,979 A | 7/1996 | Yahiaoui | |
| 5,560,794 A | 10/1996 | Currie et al. | |
| 5,611,879 A | 3/1997 | Morman | |
| D381,230 S | 7/1997 | Gifford | |
| 5,674,590 A | 10/1997 | Anderson et al. | |
| D386,571 S | 11/1997 | Wilhelm | |
| 5,706,950 A | 1/1998 | Houghton | |
| 5,712,012 A | 1/1998 | Forman et al. | |
| 5,733,629 A | 3/1998 | Insley | |
| 5,750,444 A | 5/1998 | Jarrell | |
| 5,766,389 A | 6/1998 | Brandon et al. | |
| 5,782,819 A | 7/1998 | Tanzer et al. | |
| 5,834,104 A | 11/1998 | Cordani | |
| D402,841 S | 12/1998 | Dobbs | |
| 5,852,838 A | 12/1998 | Johnson | |
| 5,853,859 A | 12/1998 | Levy et al. | |
| 5,885,418 A | 3/1999 | Anderson et al. | |
| 5,901,706 A | 5/1999 | Griesbach et al. | |
| 5,904,971 A | 5/1999 | Anderson et al. | |
| D414,252 S | 9/1999 | Orr | |
| 5,948,707 A | 9/1999 | Crawley et al. | |
| 5,961,216 A | 10/1999 | Quinn et al. | |
| 6,004,307 A | 12/1999 | Colon et al. | |
| D424,357 S | 5/2000 | Fujihara et al. | |
| D424,857 S | 5/2000 | Fujihara et al. | |
| 6,075,179 A * | 6/2000 | McCormack et al. | 604/367 |
| D428,293 S | 7/2000 | Williams | |
| 6,103,061 A | 8/2000 | Anderson | |
| 6,138,278 A | 10/2000 | Taylor | |
| 6,174,581 B1 | 1/2001 | Barker | |
| 6,245,697 B1 | 6/2001 | Conrad et al. | |
| 6,295,658 B1 | 10/2001 | Jenkins | |
| 6,298,509 B1 | 10/2001 | Vickers | |
| 6,315,864 B2 | 11/2001 | Anderson | |
| 6,327,726 B1 | 12/2001 | Weber | |
| 6,405,394 B1 | 6/2002 | Rosenberg | |
| 6,423,180 B1 | 7/2002 | Behnke et al. | |
| 6,446,275 B1 | 9/2002 | Wright et al. | |
| D464,519 S | 10/2002 | Fernando | |
| D467,116 S | 12/2002 | Mendis | |
| 6,652,947 B2 | 11/2003 | Sweeney et al. | |
| D487,663 S | 3/2004 | Bourget | |
| D487,664 S | 3/2004 | Bourget | |
| D489,560 S | 5/2004 | Bourget | |
| 6,763,531 B1 | 7/2004 | Huffman et al. | |
| 2001/0033914 A1 | 10/2001 | Walker et al. | |
| 2002/0076570 A1 | 6/2002 | Stickler | |
| 2002/0124313 A1 | 9/2002 | Cook et al. | |
| 2002/0137421 A1 * | 9/2002 | Deroches et al. | 442/411 |
| 2002/0142125 A1 | 10/2002 | Seal | |
| 2002/0166172 A1 | 11/2002 | Rosenberg | |
| 2003/0232556 A1 * | 12/2003 | Toro et al. | 442/286 |

FOREIGN PATENT DOCUMENTS

| | | | |
|---|---|---|---|
| EP | 0 218 568 B1 | 4/1990 | |
| EP | 0 556 996 B1 | 7/1997 | |
| EP | 0 920 818 A2 | 6/1999 | |
| EP | 1 199 159 A1 * | 4/2002 | B32B/27/08 |
| EP | 0 920 819 B1 | 4/2003 | |
| FR | 2760618 | 9/1998 | |
| GB | 2 124 472 A | 2/1984 | |
| GB | 2206275 | 1/1989 | |
| JP | 05-161575 A | 6/1993 | |
| JP | 07-213458 A | 8/1995 | |
| JP | 08-024165 A | 1/1996 | |
| JP | 08-164094 A | 6/1996 | |
| JP | 09-140634 A | 6/1997 | |
| JP | 10-052384 A | 2/1998 | |
| JP | 11-000288 A | 1/1999 | |
| JP | 11-285458 A | 10/1999 | |
| JP | 11-318767 A | 11/1999 | |
| JP | 2000-83868 A | 3/2000 | |
| JP | 2000-107086 A | 4/2000 | |
| JP | 2000-287881 A | 10/2000 | |
| JP | 2001-046281 A | 2/2001 | |
| JP | 2001-128898 A | 5/2001 | |
| JP | 2001-149272 A | 6/2001 | |
| JP | 2001-258801 A | 9/2001 | |
| JP | 2002-165729 A | 6/2002 | |
| JP | 2002-209799 A | 7/2002 | |
| JP | 2002-238807 A | 8/2002 | |
| JP | 2002-248068 A | 9/2002 | |
| JP | 2002-336164 A | 11/2002 | |
| JP | 2003-024247 A | 1/2003 | |
| JP | 2003-334149 A | 11/2003 | |
| JP | 2004-016301 A | 1/2004 | |
| JP | 2004-065757 A | 3/2004 | |
| WO | WO 98/22280 A1 | 5/1998 | |
| WO | WO 98/56304 A1 | 12/1998 | |
| WO | WO 00/56260 A1 | 9/2000 | |
| WO | WO 01/49151 A1 | 7/2001 | |
| WO | WO 01/60214 A2 | 8/2001 | |
| WO | WO 01/60304 A1 | 8/2001 | |
| WO | WO 03/009727 A1 | 2/2003 | |
| WO | WO 03/056979 A1 | 7/2003 | |
| WO | WO 04/021846 A1 | 3/2004 | |

OTHER PUBLICATIONS

INDA Standard Test Method IST 70.4 (99), "Standard Test Method for Water Vapor Transmission Rate Through Non Woven and Plastic Film Using a Guard Film and Vapor Pressure Sensor," Copyright 1995, 7 pages.

American Society for Testing Materials (ASTM) Designation: D 1388–96, "Standard Test Method for Stiffness of Fabrics," pp. 313–318, published Jun. 1996.

* cited by examiner

NON-SLIP ABSORBENT ARTICLE

BACKGROUND OF THE INVENTION

Absorbent articles, such as bed pads, are commonly used in hospitals, long term care facilities, and private homes to protect bedding, mattresses, cushions, seats and so forth, from being soiled by an individual. Oftentimes, however, these articles bunch, twist, wrinkle, and slide as the person moves about, particularly while sleeping. This renders the absorbent articles ineffective, makes them uncomfortable to lie or sit on, and the wrinkles can cause degradation of compromised fragile skin. In addition, absorbent articles used to protect surfaces from damage, such as tablecloths or drop cloths, are more effective when they stay securely in place. As a result, there is a need to devise a method to improve the positioning and securing of absorbent articles.

Absorbent articles, such as bed pads, typically include a liquid-impermeable bottomsheet to prevent fluids from coming into contact with surfaces beneath the absorbent article. Frequently used liquid-impermeable materials for the bottomsheet can include plastic films composed of polymers such as polypropylene or polyethylene. Such materials are not vapor-permeable. As such, comfort of the absorbent article is compromised because individuals using the absorbent article will sweat or perspire at skin locations in contact with the absorbent article while using the absorbent article. Excessive perspiration can compromise the individual's skin leading to bedsores and other skin aliments. Therefore, there is also a need for an improved absorbent article, which increases an individual's comfort while using the absorbent article.

SUMMARY OF THE INVENTION

The present invention provides a solution to securing an absorbent article while increasing the comfort of the absorbent article. Unexpectedly, it has been found that when a non-adhesive skid resistant coating is applied to a vapor-permeable yet liquid-impermeable material, the material retains sufficient breathability to provide user comfort. Also unexpectedly, the non-adhesive coating has a suitable coefficient of friction to secure the absorbent article while in use. Such a coating, unlike ordinary tape, does not leave residue on surfaces or damage surfaces when removing the adhesive, and requires no preparation by the user.

Hence in one aspect, the invention resides in an absorbent article that includes: a vapor-permeable liquid-impermeable bottomsheet having an interior surface and an exterior surface; an absorbent structure positioned adjacent the interior surface; and a non-adhesive skid-resistant coating applied to the exterior surface such that the bottomsheet remains vapor-permeable after application of the coating.

In another aspect the invention resides in an absorbent article that includes: a liquid permeable topsheet having a first surface, a second surface, and a perimeter; an absorbent structure positioned adjacent the first surface; a vapor-permeable liquid-impermeable bottomsheet having an interior and an exterior surface, the interior surface positioned adjacent the absorbent structure sandwiching the absorbent structure between the topsheet and the bottomsheet; a non-adhesive skid-resistant coating applied to the exterior surface such that the bottomsheet remains vapor-permeable after application of the coating; and a barrier means for minimizing leakage along at least a portion of the perimeter.

In an additional aspect, the invention resides in an absorbent article that includes: a liquid-permeable topsheet having a first surface, a second surface, and a perimeter; an absorbent structure joined to the first surface; a vapor-permeable liquid-impermeable bottomsheet having an interior and an exterior surface, the interior surface joined to the absorbent structure; a non-adhesive skid-resistant coating applied to the exterior surface such that the bottomsheet remains vapor-permeable after application of the coating; and a portion of the bottomsheet extending past the perimeter, and the bottomsheet portion being joined to the second surface forming an edge dam.

BRIEF DESCRIPTION OF THE DRAWINGS

The above aspects, and other features, aspects, and advantages of the present invention will become better understood with regard to the following description, appended claims, and accompanying drawings where:

DEFINITIONS

As used herein "joined" includes configurations where one element is directly or indirectly attached to another element by any means including, but not limited to, adhesives, thermal bonding, sonic bonding, chemical bonding, mechanical bonding, pressure bonding, stitching, hydrogen bonding, fasteners, or other means known to those skilled in the art. By "indirectly joined" it is meant one element is attached to a second element by one or more intermediate members. For instance, the outer-layers in an ordinary plywood laminate are indirectly joined to each other by the laminate's intermediate layers.

As used herein "laminate" refers to a structure comprising two or more layers joined together. A laminate can be constructed by joining layers of the same material together: One common example is an ordinary plywood laminate. A laminate can also be constructed by joining layers of different materials together: One common example is the wax-coated cardboard laminate used for milk cartons.

As used herein "non-adhesive" means a material that has a peel force of less than about 10 grams as determined by the following test procedure. The peel force is the average force as recorded by a tensile tester using a 51 mm gage length at a cross-head speed of 500 mm/min recorded between the interval of 25 mm to 100 mm of cross-head travel. Prior to testing, the non-adhesive surface should be been placed in contact with a dyed cotton fabric strip, such as that used for a bed sheet and heated in an oven. Strips of the absorbent article and the cotton fabric are cut to a size of 76 mm×127 mm. The cotton strip is placed onto the absorbent article strip, the strips aligned, and then weighted on one end with a 51 mm×76 mm×13 mm brass weight weighing approximately 409 grams. Ensure the portions of the strips not loaded by the weight are not in contact. Thus, the load pressing the cotton strip onto the article's coated surface is approximately 0.15 psi or 1.0 kPA. The brass weight is heated to 40.6° C. prior to weighting the specimen. The brass weight and the specimen are placed into an oven at 40.6° C. The oven should contain a heated level solid metal plate of a larger dimension than the brass weight for the specimen to rest on. The specimen is heated for 1 hour. The peel adhesion test is performed after the specimen has cooled for at least 45 minutes, but not more than two hours. The unweighted end of the cotton strip is placed into one of the tester's jaws and the end of the absorbent article strip placed into the other jaw. The average tensile force to pull the cotton strip and the absorbent article apart is then recorded by the tester over the above recited test portion. Samples must be conditioned to, and test equipment located in a laboratory atmosphere of 23±2° C. and 50±5% relative humidity when testing for 180° peel force.

As used herein "substantially liquid-impermeable" means a material, as tested by a hydrohead, which is capable of supporting of at least about 20 cm of water without substantial leakage therethrough. A suitable technique for determining the resistance of a material to liquid penetration is Federal Test Methods Standard No. 191A Method 5514—"Water Resistance Of Cloth; Low Range" dated Jul. 20, 1978.

As used herein "vapor-permeable" means the material permits the transmission of water vapor and other gases. Vapor-permeable or "breathable" materials will have a water vapor transmission rate (WVTR) of about 300 grams of $H_2O/m^2/24$ hours as tested by the WVTR test method discussed herein later.

DETAILED DESCRIPTION OF THE DRAWINGS

Figure 1:
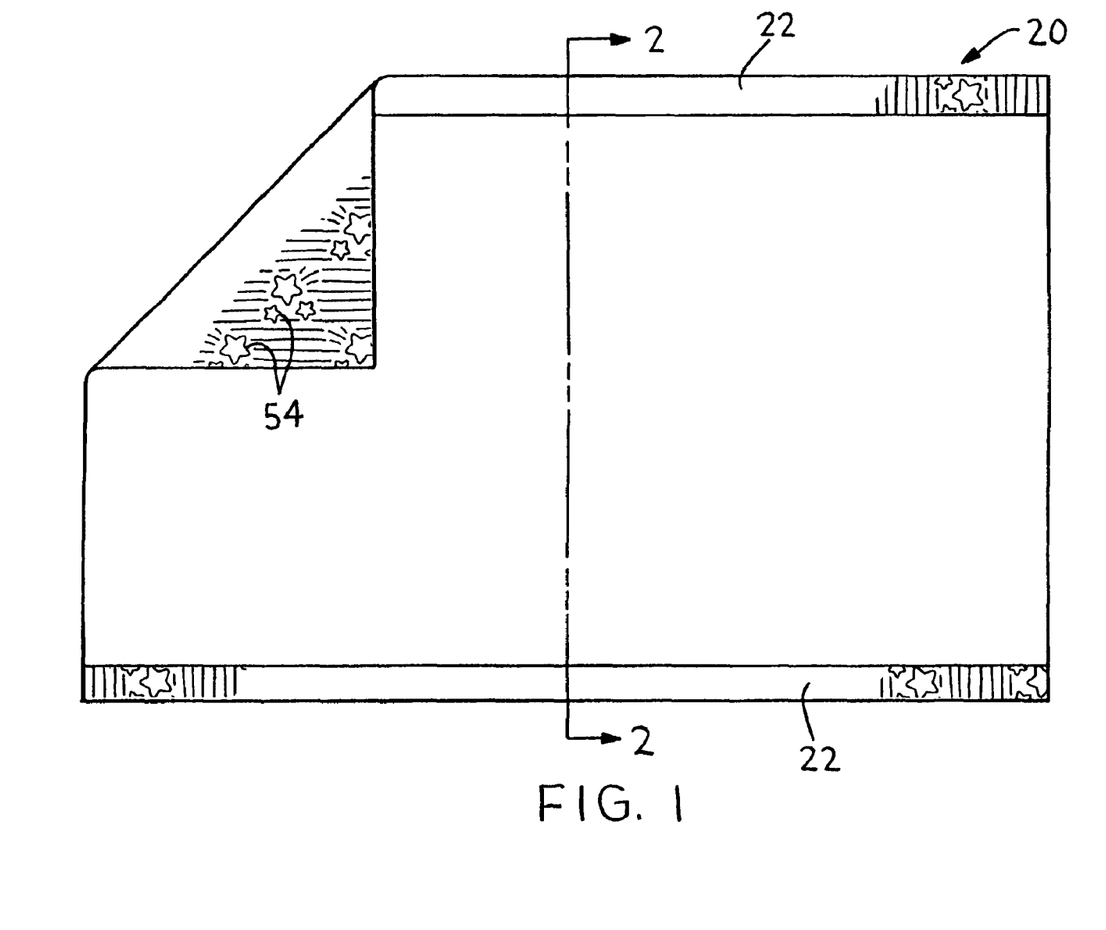
FIG. 1 illustrates a top view of one embodiment of the absorbent article with a portion of the article folded over.

Referring now to FIG. 1, an absorbent article 20 is illustrated. The absorbent article 20 is useful for the following applications without limitation: as a bed pad, a baby changing pad, a bib, a table cloth, or a painter's drop cloth. The absorbent article 20 has a generally rectangular shape, although the absorbent article 20 can be any shape or size, with the specific application for the absorbent article 20 determining the appropriate size and shape. The absorbent article can be sized to cover extremely large areas such as floors or gymnasiums. Preferably the absorbent article has an area greater than 100 square inches (15.5 cm²), more preferable the absorbent article has an area greater than 400 square inches (62 cm²), and most preferred the absorbent article has an area greater than about 800 square inches (124 cm²).

The absorbent article 20 includes a barrier means 22 for minimizing leakage located adjacent the rectangle's dimensionally longer sides. However, the barrier means 22 can be located adjacent all of the absorbent article's sides or adjacent only a portion of any side. Alternative embodiments for the barrier means 22 will be discussed in more detail later. The absorbent article is a laminate of several layers joined together. The absorbent article also contains a plurality of rugosities 54 on the bottomsheet of the absorbent article as shown in the folded over portion.

Figure 2:
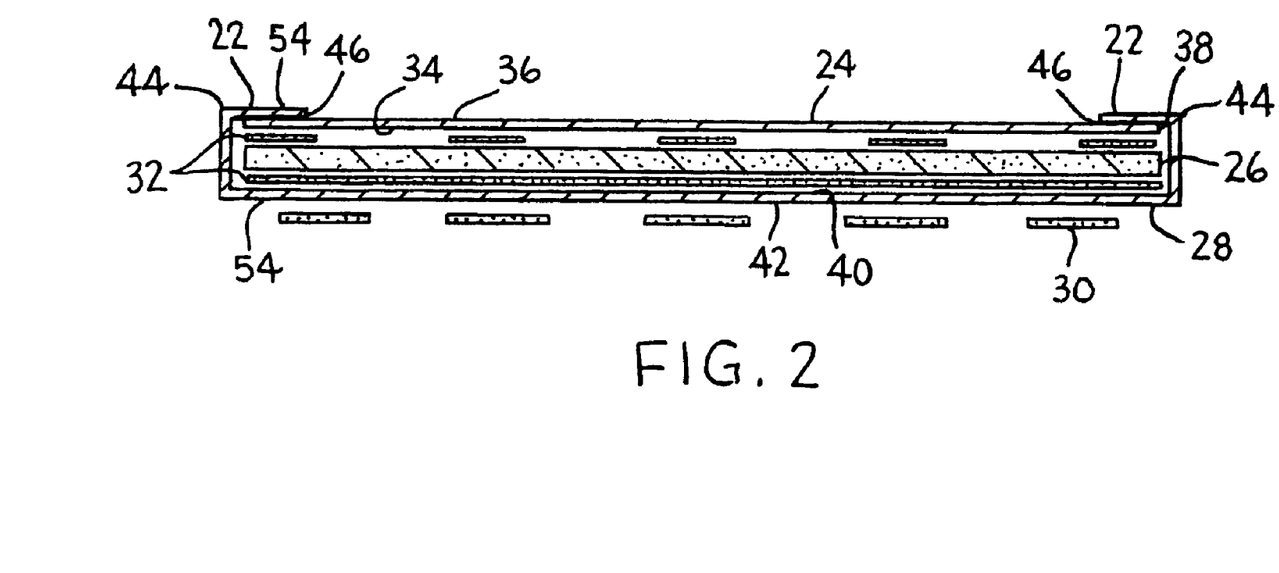
FIG. 2 is a cross-section view of the absorbent article of FIG. 1 taken along line 2—2.

Referring now to FIG. 2, a schematic cross-section taken along line 2—2 of FIG. 1 is illustrated. The various layers of the laminate can include a topsheet 24, an absorbent structure 26, a bottomsheet 28, a non-adhesive skid resistant coating 30, and an adhesive 32 joining the topsheet 24, the absorbent structure 26, and the bottomsheet 28 together. Alternatively, the adhesive 32 can join only the topsheet 24 and absorbent structure 26, only the bottomsheet 28 and the absorbent structure 26, or the adhesive 32 can be eliminated and other means known to those of skill in the art employed to secure the layers of the absorbent article 20 together.

The topsheet 24 has a first surface 34, a second surface 36, and a perimeter 38. The first surface 34 is positioned adjacent the absorbent structure 26. The topsheet 24 is not essential to the absorbent article, and an absorbent article with only the bottomsheet 28 and the absorbent structure 26 is within the scope of the invention. The nature of the absorbent structure 26 will determine if the topsheet 24 is required. For instance, if the absorbent structure 26 is a loose fibrous wood pulp, the topsheet 24 will assist in retaining the absorbent structure 26. Alternatively, if the absorbent structure 26 is an air laid or coform material, the absorbent structure 26 can have sufficient integrity to be utilized without the topsheet 24.

The topsheet 24, when present, affords a body-facing surface which is compliant, soft feeling, and nonirritating to the wearer's skin. Further, the topsheet 24 can be less hydrophilic than the absorbent structure 26, and is sufficiently porous to be liquid permeable, permitting liquid to readily penetrate through its thickness to reach the absorbent structure 26. A suitable topsheet 24 can be manufactured from a wide selection of web materials, such as porous foams, reticulated foams, apertured plastic films, natural fibers (for example, wood or cotton fibers), synthetic fibers (for example, polyester, polyethylene, or polypropylene fibers), or a combination of natural and synthetic fibers.

The topsheet 24 is typically employed to help isolate the wearer's skin from liquids held in the absorbent structure 26. Various woven and nonwoven fabrics can be used for the topsheet 24. For example, the topsheet 24 can be composed of a meltblown or spunbonded web of desired fibers, and can also be a bonded-carded-web. The various fabrics can be composed of natural fibers, synthetic fibers or combinations thereof and used for the topsheet 24. For the purposes of the present description, the term "nonwoven web" means a web of fibrous material, which is formed without the aid of a textile weaving or knitting process. The term "fabrics" is used to refer to all of the woven, knitted and nonwoven fibrous webs. The fabrics can be composed of a substantially hydrophobic material, and the hydrophobic material can optionally be treated with a surfactant or otherwise processed to impart a desired level of wettability and hydrophilicity.

In a particular embodiment of the invention, the topsheet 24 was a nonwoven, spunbond polypropylene fabric composed of about 2.8–3.2 denier fibers formed into a web having a basis weight of about 22 gsm and density of about 0.06 gm/cc. The fabric was surface treated with an operative amount of surfactant Ahcovel Base N62 available from Hodgson Chemicals Incorporated having an office in Oak Creek, Wis. The surfactant was applied at an addition rate of 0.28% by weight. The surfactant can be applied by any conventional means, such as spraying, printing, brush coating or the like.

Referring to FIG. 2, the absorbent structure 26 provides a repository for holding and storing absorbed liquids and other waste materials. The absorbent structure 26 can include an absorbent pad composed of selected hydrophilic fibers and optionally high-absorbency particles (superabsorbents). The absorbent structure 26 is positioned adjacent the bottomsheet 28, and is sandwiched between the bottomsheet 28 and the topsheet 24 if present. It should be understood that the absorbent structure 26 can comprise a single, integral piece of material, or alternatively, can comprise a plurality of individual separate pieces of material or components, which are operably assembled together.

Various types of wettable, hydrophilic fibrous material can be used to form the component parts of the absorbent structure 26. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers can be hydrophilized, for example, by treatment with silica, treatment with a material that has a suitable hydrophilic moiety and is not readily removable from the fiber, or by sheathing the nonwettable, hydrophobic fiber with a hydrophilic polymer during or after the formation of the fiber.

For the purposes of the present invention, it is contemplated that selected blends of the various types of fibers mentioned above can also be employed. As used herein, the term "hydrophilic" describes fibers or the surfaces of fibers, which are wetted by the aqueous liquids in contact with the fibers. The degree of wetting of the materials can, in turn, be described in terms of the contact angles and the surface tensions of the liquids and materials involved. A SFA-222 Surface Force Analyzer System, available from Cahn Instruments having an office in Wethersfield, Conn., or a substantially equivalent system can provide quantitative results for measuring the wettability of particular fiber materials or blends of fiber materials. When measured with such system, fibers having contact angles less than 90° are designated "wettable", while fibers having contact angles greater than 90° are designated "nonwettable".

The absorbent structure 26 can comprise a matrix of hydrophilic fibers, such as a web of cellulosic fluff, mixed with particles of high-absorbency material. In particular arrangements, the absorbent structure 26 can comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles can be substantially homogeneously mixed with the hydrophilic fibers, or can be non-uniformly mixed. For example, the concentrations of superabsorbent particles can be arranged in a gradient through a substantial portion of the thickness (z-direction) of the absorbent structure 26, with lower concentrations toward the topsheet 24 and relatively higher concentrations toward the bottomsheet 28. Alternatively, the concentrations of superabsorbent particles can be arranged in a gradient, through a substantial portion of the thickness (z-direction) of the absorbent structure 26, with higher concentrations toward the topsheet 24 and relatively lower concentrations toward the bottomsheet 28. The superabsorbent particles can also be arranged in a generally discrete layer within the matrix of hydrophilic fibers. In addition, two or more different types of superabsorbents can be selectively positioned at different locations within or along the fiber matrix.

The high-absorbency material can comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alphaolefins, poly(vinyl pyrrolidone), poly(vinylmorpholinone), poly(vinyl alcohol), and mixtures and copolymers thereof. Further polymers suitable for use in the absorbent structure 26 include natural and modified natural polymers, such as hydrolyzed acrylonitrilegrafted starch, acrylic acid grafted starch, methylcellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention.

In a particular embodiment of the invention, the absorbent structure 26 was a 75 gsm basis weight coform material having 75% wood pulp fibers, and 25% polypropylene fibers. Coform is available from Kimberly-Clark Corporation having an office in Neenah, Wis.

Referring to FIG. 2, the bottomsheet 28 has an interior surface 40 and an exterior surface 42. The bottomsheet 28 is positioned such that the interior surface 40 is adjacent the absorbent structure 26. The bottomsheet 28 is selected from a breathable material that is vapor-permeable, but substantially liquid-impermeable. Such materials are typically microporous, which permit gases, such as water vapor, to pass through the bottomsheet 28 while substantially preventing liquids from passing through the bottomsheet. Breathability of the bottomsheet 28 greatly adds to an individual's comfort when lying or sitting on the absorbent article 20 for extended periods of time, and permits perspiration to pass though the absorbent article. In addition, the bottomsheet 28 substantially prevents liquids contained in the absorbent structure 26 from wetting items in contact with the absorbent article 20, such as bed sheets, cushions, floors, or furniture.

The bottomsheet 28 can include more than one layer such as a nonwoven fabric layer laminated to a polymer film layer, that is vapor-permeable. One example being a stretch thinned or stretch thermal laminate material composed of a 0.6 mil (0.015 mm) thick polypropylene blown film and a 0.7 ounce per square yard (23.8 gsm) polypropylene spunbond material (2 denier fibers). A complete description of the material is found in U.S. Pat. No. 6,075,179 issued Jun. 13, 2000 to McCormick et al. entitled "Low Gauge Films And Film/Nonwoven Laminates, which is hereby incorporated by reference. A material of this type forms the outer cover of a HUGGIES® SUPREME® diaper, which is commercially available from Kimberly-Clark Corporation having an office in Neenah, Wis.

Alternatively, the vapor-permeable bottomsheet 28 can be composed of a single microporous polymer film or a nonwoven fabric layer that has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn.

In a particular embodiment of the invention, the bottomsheet 28 was RM 1976-008 which is a highly breathable stretched thermal laminate (HBSTL) having a 1.15 osy (51 gsm) basis weight. HBSTL has a minimum vapor-permeability of at least 6,400 grams $H_2O/m^2/24$ hours, and a minimum hydrohead of at least 60 cm. HBSTL is available from Kimberly-Clark Corporation having offices in Neenah, Wis.

As illustrated by FIG. 2, a non-adhesive skid resistant coating 30 is applied to the exterior surface of the bottomsheet 28. Generally, the coating 30 is applied to a large portion of the exterior surface. However, depending on the absorbent article's size and the anti-skid properties of the coating 30 utilized, it can be necessary to only coat a portion of the bottomsheet 28. The coating 30 can be utilized either as the absorbent article's only placement system, or in combination with other attachment means such as adhesives, tape, clips, refastenable members, buttons, holders, and the like. For instance, a small area of attachment adhesive could be utilized in order to hold each corner of the absorbent article 20, while the coating 30 secures the remainder of the absorbent article 20.

The materials suitable for the coating 30 can be any latex or hot melt that has sufficient skid-resistant properties (coefficient of friction) to resist movement of the absorbent article 20 during use, while simultaneously being non-adhesive as previously defined. The static coefficient of friction (COF) of the absorbent article 20 as measured by the test method described herein later is desirably greater than about 0.7. More desirable, the COF is greater than about 1.0. More desirable yet, the COF is greater than about 1.2, and most desirable the COF is greater than about 1.5.

The coating 30 should present a generally uniform thickness after application to the absorbent article 20, and should not render the bottomsheet 28 vapor-impermeable. Preferably, the WVTR of the bottomsheet after application of the coating is greater than about 300 grams of $H_2O/m^2/24$ hours. More preferable, the WVTR of the bottomsheet after application of the coating is greater than about 1000 grams of $H_2O/m^2/24$ hours. Most preferable, the WVTR of the bottomsheet after application of the coating is greater than about 5,000 grams of $H_2O/m^2/24$ hours The coating 30 can be any suitable composition, which is non-adhesive while having adequate skid-resistant properties including but not limited to: amorphous olefin polymers; urethane; copolymers; interpolymers including especially polyethylene, polypropylene, ethylene propylene copolymers, propylene 1-butene copolymers, propylene 1-hexene copolymers; higher propylene; ethylene 1-alkene copolymer; terpolymer analogs; ethylene vinyl acetate copolymers (applied as either a hot melt or water based coating), especially those having at least 28% vinyl acetate; polyvinyl acetate (normally used in water-based emulsions); styrene-butadiene (applied in an emulsion or as a hot melt); cellulose acetate butyrate (normally hot melt coatings); ethyl cellulose (normally blended with a plasticizer and a resin and applied as a hot melt); acrylics (normally emulsion systems that are not blended); synthetic rubber hot melt (including KRAYTON® or DEXCO®, block copolymers having elastomeric and styrenic blocks, rubber, resin, plasticizer blends); other hot melts (polyethylenes alone or blended, or polyamides).

Typical of such compositions are the lower crystallinity amorphous olefin polymers and copolymers, ethylene-vinyl acetate copolymers, acrylic terpolymers containing acrylic acid and methacrylic acids, acrylic copolymers, ethylene-vinyl acetate/resin latex emulsions, ethylene-vinyl acetate hot-melt adhesives, synthetic rubber (block copolymers with elastomeric and styrenic components) hot melt adhesives, and polyvinyl acetate/resin emulsions. Such materials are available from H. B. Fuller Company, E. I. DuPont, Exxon, Mobil, Huntsmann Polymers, National Starch and Chemists, and Bostick-Findley Adhesives, among others. The above description has been intended to be illustrative rather than exhaustive of the possibilities of the invention.

The coating can be applied by any means, including without limitation, spraying; brushing; any commercial coating method including offset, gravure, blade, slot, extrusion, or rod; dipping; or sponging. The coating can only cover a portion of the absorbent article or can cover the entire surface of the bottomsheet 28 in any manner as long as the bottomsheet 28 remains vapor-permeable. The coating can be applied in number of different patterns or stripes to achieve this effect or via spraying of the entire exterior surface.

In a particular embodiment, the coating 30 was an ethylene copolymer RT 2315 available from Huntsman Corporation having an office in Houston, Tex. The coating was applied to the bottomsheet 28 using a spray applicator. Different embodiments of the non-slip absorbent article 20 were made at addition rates of 6 gsm, and 8 gsm of RT 2315 to the bottomsheet 28.

Referring specifically to the bottomsheet 28, the exterior surface 42 can be non-planar and contain a plurality of rugosities 54, as shown in FIGS. 1 and 2, or the exterior surface 42 can be planar (not shown). Unexpectedly, the applicants have found that when the exterior surface 42 is non-planar, the skid resistance of the absorbent article 20 is improved after application of the coating 30. This improves the ability of the absorbent 20 to remain in position during use.

A non-planar exterior surface 42 can be produced by any number of methods known to those of skill in the art. For instance, a non-planar exterior surface 42 can be produced by micro-creping or creping the bottomsheet 28 to produce a plurality of rugosities 54 in the exterior surface 42. Alternatively, using any embossing method on the bottomsheet 28 will produce a pattern in the bottomsheet 28 creating a non-planar exterior surface 42 with rugosities 54. Alternatively, the non-planar exterior surface 42 could be formed into the bottomsheet 28 during manufacturing by the laminating step in the production of breathable laminates as described in U.S. Pat. No. 6,075,179, previously incorporated by reference. As discussed in the patent, the individual webs are sent though a two-roll nip wherein one or both of the rolls are heated. Typically, one roll is smooth and the other patterned, which results in a bottomsheet 28 having a planar interior surface 40 and a non-planar exterior surface 42. The planar interior surface 42 can be readily joined to the absorbent structure 26 by adhesive 32.

The non-planar exterior surface 42 improves the flexibility and drape of the absorbent article 20. Thus, the absorbent article 20 becomes more cloth-like in its drape and feel, and the absorbent article is more like a blanket than a plastic sheet. Drape of the absorbent article 20 is an important consideration in comfort, resisting movement during use, and for providing a quieter absorbent article during use. The non-planar exterior surface 42 also improves the absorbent article's softness perception and hand feel, which can be diminished or stiffened by application of the coating 30. The stiffness of the absorbent article can be tested using the Drape Stiffness test method discussed in the test methods section. Preferably, the drape stiffness of the absorbent article is less than about 10 cm, more preferable the drape stiffness is less than about 7 cm, and most preferred the drape stiffness is less than about 5 cm.

The stiffness of an absorbent article is also often a function of the thickness of the absorbent article. Thus, thinner absorbent articles generally are less stiff than thicker absorbent articles, and are consumer preferred if they meet or exceed the performance of the thicker articles. The thickness of the absorbent article is tested using the test discussed in the test methods section. Preferably, the absorbent article has a thickness less than about 15 mm, more preferable the thickness is less than about 10 mm, and most preferred the thickness is less than about 5 mm.

Referring now to FIG. 2, the barrier means 22 is constructed by extending the bottomsheet 28 past the perimeter 38 of the topsheet 24, folding the bottomsheet 28 onto the topsheet 24 forming at least one fold 44, and then joining the bottomsheet 28 to the topsheet 24 to form an edge dam 46. The edge dam 46 minimizes the leakage of fluids past the perimeter 38 by retaining or directing the fluids into the absorbent structure 26.

Figure 3:
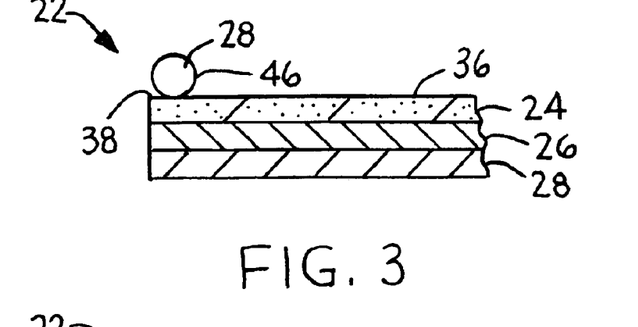
FIG. 3 is a partial cross-section view illustrating another embodiment for the barrier means.

Referring now to FIGS. 3–6 alternative barrier means 22 are illustrated in partial cross-section views with like numerals referring to previously described elements. FIG. 3 illustrates a second embodiment for the barrier means 22. The barrier means 22 can include a strip of material 48 joined to the second surface 36 at a location adjacent the perimeter 38 to form the edge dam 46. The strip 48 can have any cross-section, including without limitation, circular, rectangular, square, or oval. The strip 48 can be composed of any material useful to those of skill in the art to prevent or minimize fluid leakage past the perimeter 38. The strip 48 minimizes leakage of fluids past the perimeter 38 by retaining or directing the fluids into the absorbent structure 26.

Figure 4:
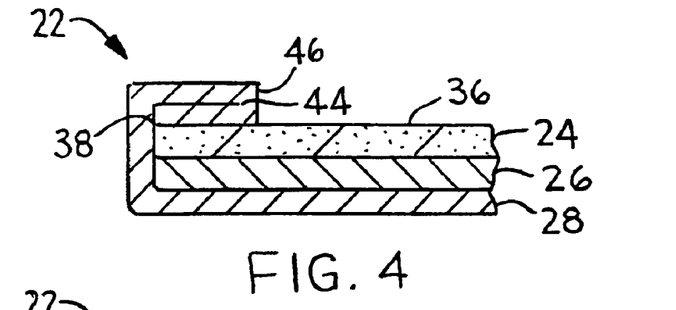
FIG. 4 is a partial cross-section view illustrating another embodiment for the barrier means.

FIG. 4 illustrates a third embodiment for the barrier means 22. This embodiment is similar to the embodiment shown in FIG. 2, but includes two or more folds 44 in the bottomsheet 28 adjacent the perimeter 38. Thus, the bottomsheet 28 is folded over multiple times prior to joining the bottomsheet 28 to the topsheet 24 forming the edge dam 46. In the illustrated embodiment, the bottomsheet 28 was folded twice, creating two folds 44 prior to joining the bottomsheet 28 to the topsheet 24. If desired, the bottomsheet 28 can be folded three, four, five, or any number of folds prior to joining the bottomsheet 28 to the topsheet 24. By increasing the number of folds, the height of the edge dam 46 is increased enhancing containment of fluids and assisting in minimizing leakage past the perimeter 38.

Figure 5:
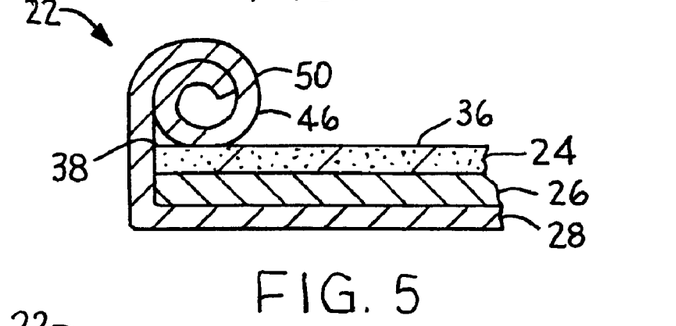
FIG. 5 is a partial cross-section view illustrating another embodiment for the barrier means.

FIG. 5 illustrates a fourth embodiment for the barrier means 22. In this embodiment, the bottomsheet 28 extends past the topsheet 24, the extended portion is wound into a roll 50, and then the wound roll 50 is joined to the topsheet 24 forming the edge dam 46. Similar to the other structures previously described, the roll 50 joined to the topsheet 24 creates the edge dam 46 resulting in the barrier means 22 that minimizes leakage of fluids past the perimeter 38 or directs the fluids into the absorbent structure 26.

Figure 6:
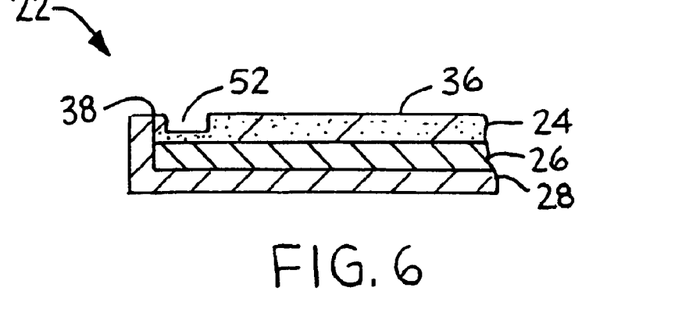
FIG. 6 is a partial cross-section view illustrating another embodiment for the barrier means.

FIG. 6 illustrates a fifth embodiment for the barrier means 22. In this embodiment, a gutter 52 is formed into the topsheet 24 near the perimeter 38. The gutter 52 serves to collect fluids near the perimeter 38 and redirect them into the absorbent structure 26 minimizing leakage past the perimeter 38. The gutter 52 can be formed by mechanical embossing, thermal embossing, removal of material, or other means known to those of skill in the art.

FIGS. 3–6 show alternative embodiments for the barrier means 22 with an absorbent article 20 utilizing topsheet 24. It is within the scope of the invention that similar barrier means 22 can be employed with an absorbent article 20 constructed without a topsheet 24 having only an absorbent structure 26 and a bottomsheet 28. Thus, several barrier means 22 for minimizing leakage are shown and can be utilized with either single layer or multi-layer absorbent articles. Such barrier means 22 can include without limitation, a strip, one or more folds, a roll, a gutter, an edge dam, or any other means that minimizes leakage of fluids past the perimeter 38.

TEST METHODS

Drape Stiffness

Drape Stiffness is tested using ASTM Standard Test D 1388 "Stiffness of Fabrics." The specimen size for this test is changed from 1"×6" (2.54 cm×15.24 cm) to 1" by 8" (2.5 cm×20.3 cm). Otherwise, the test method outlined in ASTM D 1388 is followed. A summary of the test method follows.

The test determines the bending length of an absorbent article or fabric, using the principle of cantilever bending of the specimen under its own weight. This method measures the drape stiffness or resistance to bending of the specimen. The bending length is a measure of the interaction between specimen weight and specimen stiffness as shown by the way in which a specimen bends under its own weight. This is a reflection of the stiffness of the specimen when bent in one plane under the force of gravity.

The 1"×8" (2.5 cm×20.3 cm) specimen is slid, at 4¾ in. per minute (12.1 cm/min), in a direction parallel to its long dimension, so that its leading edge projects from the edge of a horizontal surface. The length of the overhang is measured when the tip of the specimen is depressed under its own weight to the point where the line joining the tip to the edge of the platform makes a 41.5° angle with the horizontal. The longer the overhang the slower the specimen was to bend; thus, higher numbers indicate a stiffer specimen.

The following apparatus and materials are required: FRL-Cantilever Bending Tester, Model 79-10 available from Testing Machines Inc, 400 Bayview Avenue, Amityville, N.Y. 11701; Cutting Press with 1"×8" (2.5 cm×20.3 cm) rectangular cutting die.

The specimen should be prepared as follows: Testing equipment should be located in, and samples conditioned to, an atmosphere of 23±2° C. and 50±2% relative humidity.

Handle the specimens as little as possible to avoid getting oil, grease, water, etc. on them, which would bias the test results. In particular, avoid touching the surface of the specimens. Specimens should be evenly spaced across the cross directional width of the sample. Cut 5 specimens in each of the machine and cross directions from each sample; i.e., a total of 10 specimens are required for each sample. Specimens should be cut from areas free of folds.

The specimens should be tested as follows: Calibrate the test equipment according to the manufacture's directions prior to testing the specimens. After lifting the movable slide up, place the specimen on the stationary table with the coated side up. The length of the specimen should be parallel to the edge of the table. The edge of the specimen should be aligned with the line scribed ¼" from the right hand edge of the table. Lower the movable slide back onto the stationary table being careful not to move the specimen. Verify that the bend angle indicator is at the 41.5° angle marked on the scale. Turn the On/Off switch ON. Watch the leading edge of the specimen closely. Turn the switch OFF the instant that the edge of the specimen touches the knife-edge. Read, and record, the overhang length from the linear scale. Test remaining specimens following the above procedure.

The results of the test are reported as follows: Report the bending length recorded for each individual specimen. Specimens cut MD and CD are considered different and their results should be reported separately. Calculate the average and standard deviation of the bending length for the five specimens in each direction. This is the absorbent article bending length for that direction. Calculate the drape stiffness of the absorbent article in each direction according to the following equation:

Drape Stiffness (cm)=bending length (cm)/2

Water Vapor Transmission Rate (WVTR)

INDA standard test IST 70.4(01) "Standard Test Method for Water Vapor Transmission Rates of 500 To 100,000 gm/m$^2$ day Through Nonwoven Fabrics and Plastic Barriers" is used to determine the WVTR of the bottomsheet. The Association of the Nonwovens Fabric Industry, having offices in Cary, N.C., publishes the test method. The following is a summary of the test method.

The method is applicable to sheets and films up to 3 mm (0.1 in.) in thickness, consisting of single or multi-layer synthetic or natural polymers, nonwoven fabrics, and plastic film, including coated materials. Other tests know to those of skill in the art can be used to determine the WVTR of materials greater than 3 mm in thickness. This test is conducted using commercially available WVTR test apparatus. A dry chamber is separated from a wet chamber (filled with distilled water) of known temperature and humidity by a permanent guard film and the specimen. The dry chamber, guard film, and the wet chamber make up a diffusion cell, in which the specimen is sealed. Water vapor diffuses through the air gap and the guard film and then mixes with a dry gas flow (compressed nitrogen) flow that sweeps the guard film. The mixture is carried to a water vapor sensor that produces an electric signal, the amplitude of which is proportional to water vapor concentration. The electrical signal is routed to a computer that calculates the transmission rate of the combination of the air gap, the guard film, and the test film. The computer then further calculates the rate at which moisture is transmitted through the specimen. The WVTR is the time rate of water vapor flow normal to the surfaces, under specific steady-state conditions of temperature and humidity per unit area, reported in units of grams of $H_2O/m^2/24$ hours.

The following materials and apparatus are required: A Permatran-W model 100k WVTR tester, guard film assembly, and metal sample holder available from Mocon Modern Controls, Inc. having an office in Minneapolis, Minn. High purity level chromatograph distilled water and compressed nitrogen gas 99.7% pure or greater.

The specimens should be tested as follows: Conduct the testing in an atmosphere of 23°±2° C. and 50±2% relative humidity. Condition all specimens a minimum of 24 hours prior to testing. Using the appropriate template, knife, and cutting mat supplied with the WVTR tester cut a test specimen from the bottomsheet 28 that has been coated with the non-adhesive skid resistance coating 30. Calibrate the WVTR tester according to the manufacturer's directions. Remove the test cell clamps and the test cell head, lifting it gently of the block and observing the condition of the guard film. Ensure the guard film is free of holes, tears, or other defects. Mount the test specimen on the empty sample holder on the block. Replace the test cell head onto the sample holder and clamp in place while ensuring the knob is returned to the same position as during calibration. Start the testing. The WVTR tester will then test the specimen and report the WVTR in grams of $H_2O/m^2/24$ hours.

Coefficient of Friction (COF)

This test is used to measure the static COF of the absorbent article after application of the non-adhesive skid resistant coating. The procedure determines the initial (static) friction of a material when beginning to slide over another material. A sled, which has the test specimen attached, is pulled over a moving platen (table) that has a representative surface material attached. The test specimen and material on the platen are in surface-to-surface contact with each other. The COF is defined as the measure of the relative difficulty when the surface of one material starts to slide over an adjoining surface of either itself or of another material. The static COF represents the maximum COF values obtained during the first inch (2.5 cm) of specimen travel distance at a testing rate of six inches per minute (15.2 cm/min). It is believed the static coefficient of friction, as opposed to the kinetic coefficient of friction (average value obtained peak initial specimen movement), is more representative of the absorbent article's resistance to movement during use.

The following apparatus and material are required: Coefficient of Friction tester TMI Model 32-06 and Testing-Sled with foam 200±5.0 grams both obtained form Testing Machines, Inc., Islanda, N.Y. Cotton Fabric Bed Sheet—250 thread count, 100% Egyptian cotton such as a Willow Bay brand twin flat sheet manufactured by Spring Industries Fullerton, Calif.

The test specimens are prepared as follows: To prevent contamination of the testing material, multiple layers must be cut together (minimum of three layers). Discard the two outer layers after the inner specimen(s) have been used. Care must be taken in handling the specimens. The test surface must be kept free of all dust, lint, fingerprints, or any foreign matter that might change the surface characteristic of the coating. Identify and mark the machine direction on the test side of the specimen. Cut the sled specimen from the absorbent article 120±1 mm (4.72±0.04 in.) in the machine direction (MD) and 67±1 mm (2.64±0.04 in.) in the cross direction (CD). Make a 25.4±10 mm (1±0.39 in.) centered cut into one of the 67-mm ends of the sled specimen; this allows the specimen to fit around the guide pin on the test sled. Cut the testing bed specimen from the cotton fabric bed sheet 305±1 mm (12±0.04 in.) in the machine direction (MD) by approximately 102–127 mm (4–5 in.) wide.

The specimens are tested as follows: Conduct the testing in an atmosphere of 23°±2° C. and 50±2% relative humidity. Condition all specimens and the cotton fabric a minimum of 24 hours prior to testing. Calibrate the COF tester according the manufacturer's directions. Set the adjustable stop knob located on the back of the tester at six inches (15.2 cm) and set the travel speed to six inches per minute (15.2 cm/min). Set the COF tester display to read grams and zero the display. The absorbent article specimen with the coating surface exposed is mounted to the test sled using double-sided tape or clamps on the sled. The cotton fabric material is mounted on the testing bed using double-sided tape or clamps. Ensure the surfaces of the test specimen and test bed materials are not contaminated during mounting. The sled is positioned very lightly and gently on the surface of the moving platen to prevent any unnatural bond from developing between the exposed coating 30 and the cotton sheet. Start the test by pressing the TEST key on the COF tester.

The results are calculated and displayed by the COF tester. The COF tester records the "STATIC" value for the highest instantaneous coefficient of friction value obtained to begin the movement between the surfaces within the first inch of pull. The COF tester also records the "KINETIC" value obtained from the average of the values obtained during the 60 seconds of the test (6 inch travel distance). The calculation for "STATIC" coefficient of friction is obtained by the tester using the following equation: $\mu_s = A_s/B$, where $\mu_s$=the static coefficient of friction value, $A_s$=the maximum initial gram value obtained within the first inch of movement, and B=sled weight of about 200 grams.

Thickness

The thickness of the absorbent article is determined at a pressure of 0.2 psi (1.4 kPa) using a platten that is 3 inches (7.6 cm) in diameter. Testing equipment should be located in, and samples conditioned to, an atmosphere of 23±2° C. and 50±2% relative humidity. The absorbent article is tested after being conditioned to the test conditions for a minimum of 24 hours. The thickness is reported to the nearest 0.001 inch or 0.025 mm for each sample, and the average of ten samples is used as the thickness of the absorbent article.

EXAMPLES

A non-slip absorbent article 20 was made according the present invention using a topsheet 24 that was a nonwoven, spunbond polypropylene fabric composed of about 2.8–3.2 denier fibers formed into a web having a basis weight of about 22 gsm and density of about 0.06 gm/cc. The topsheet was treated with an operative amount of surfactant Ahcovel Base N62. The surfactant was applied at an addition rate of 0.28% by weight. Joined to the topsheet 24 was an absorbent structure 26 formed from a 75 gsm coform material having 75% wood pulp fibers, and 25% polypropylene. A bottomsheet 28 was joined the absorbent structure 26. The bottomsheet 28 was RM 1976-008 (HBSTL) having a 1.15 osy (51 gsm) basis weight. HBSTL has a minimum vapor-permeability of at least 6,400 grams of grams of $H_2O/m^2/24$ hours, and a minimum hydrohead of at least 60 cm. Applied to the exterior surface 42 was a non-adhesive skid resistant coating 30 of an ethylene copolymer RT 2315. Different embodiments of the non-slip absorbent article 20 were made at addition rates of 6 gsm, and 8 gsm of RT 2315 to the bottomsheet 28.

The bottomsheet 28 was tested for WVTR according the above test method. With 8 gsm of coating the WVTR of the bottomsheet was 10,671 grams of $H_2O/M^2/24$ hours. With 6 gsm of the coating the WVTR was 12,988 grams of $H_2O/m^2/24$ hours. Without the addition of any coating the WVTR was 13,345 grams of $H_2O/m^2/24$ hours. When the entire absorbent article with an 8 gsm coating and a 13.6 gsm spunbond topsheet was tested (specimen cut through the entire thickness), the WVTR was 9,861 grams of $H_2O/m^2/24$ hours.

The thickness of the absorbent article with the 8 gsm coating was tested and found to be 1.82 mm (0.074 inches). The drape stiffness of the absorbent article with the 8 gsm coating was tested and found to be 4.76 cm in the CD and 4.63 cm in the MD. The static COF for the absorbent article with the 6 gsm coating was tested and found to be 1.61. The static COF for the absorbent article with 8 gsm coating was tested and found to be 1.33.

A bed pad was purchased from Walgreens Drug Store in Neenah, Wis. being identified as Walgreen's Multi-Purpose Disposable Underpad. The bottomsheet of the bed pad appeared to be either polyethylene or polypropylene, and no coating was present on the bottomsheet. The static coefficient of friction COF for the bed pad when tested using the above test method was 0.50. The water vapor transmission rate for the bed pad when tested using the above test method was 0 grams of $H_2O/m^2/24$ hours.

It will be appreciated that the foregoing background, summary, and detailed description are given for the purposes of illustration, and are not to be construed as limiting the scope of this invention, which is defined by the following claims and all equivalents thereto.

We claim:

1. An absorbent article comprising:
   a vapor-permeable liquid-impermeable microporous bottomsheet having an interior surface and an exterior surface;
   an absorbent structure positioned adjacent the interior surface; and
   a non-adhesive skid-resistant coating applied to the exterior surface such that the bottomsheet remains vapor-permeable after application of the coating.

2. The absorbent article of claim 1 further comprising a liquid permeable topsheet having a first surface positioned adjacent the absorbent structure, sandwiching the absorbent structure between the topsheet and the bottomsheet.

3. The absorbent article of claim 2 wherein the absorbent structure is adhesively joined to at least one of the first surface and the interior surface.

4. The absorbent article of claim 1 wherein the bottomsheet has a vapor permeability, after application of the coating, of greater than about 300 grams $H_2O/m^2/24$ hours.

5. The absorbent article of claim 1 wherein the exterior surface, after application of the coating, has a static coefficient of friction greater than about 0.7.

6. The absorbent article of claim 1 wherein the absorbent article has a drape stiffness less than about 10 cm after application of the coating.

7. The absorbent article of claim 1 wherein the absorbent article has an area greater than about 100 square inches.

8. The absorbent article of claim 5 wherein the absorbent article has a thickness less than about 15 mm.

9. The absorbent article of claim 1 wherein the exterior surface is planer.

10. The absorbent article of claim 1 wherein the exterior surface is non-planar improving the skid-resistance of the absorbent article.

* * * * *